United States Patent [19]
Suzukamo et al.

[11] Patent Number: 4,879,429
[45] Date of Patent: Nov. 7, 1989

[54] SOLID BASE, PROCESS FOR PREPARING THE SAME AND USE OF THE SAME IN PREPARATION OF INTERNAL OLEFINS

[75] Inventors: Gohfu Suzukamo, Ibaraki; Masami Fukao, Shiga, both of Japan

[73] Assignee: Sumitomo Chemical Company, Limited, Osaka, Japan

[21] Appl. No.: 304,228

[22] Filed: Jan. 31, 1989

Related U.S. Application Data

[62] Division of Ser. No. 155,848, Feb. 16, 1988, Pat. No. 4,822,764.

[30] Foreign Application Priority Data

Feb. 16, 1987 [JP] Japan ................................. 62-32790
Feb. 16, 1987 [JP] Japan ................................. 62-32791
Feb. 16, 1987 [JP] Japan ................................. 62-32792
Feb. 16, 1987 [JP] Japan ................................. 62-32793

[51] Int. Cl.$^4$ .......................... C07C 5/25; C07C 5/23
[52] U.S. Cl. .................................... 585/670; 585/664
[58] Field of Search ............................... 585/664, 670

[56] References Cited

U.S. PATENT DOCUMENTS 3,897,509  7/1975  Nagase et al. ...................... 585/363
3,906,026  9/1975  Nagase et al. ...................... 562/506
3,928,485  12/1975 Nagase et al. ...................... 585/664
4,205,192  5/1980  Haada .
4,720,601  1/1988  Suzukamo et al. .
4,727,204  2/1988  Suzukamo et al. .

Primary Examiner—H. M. S. Sneed
Assistant Examiner—James A. Saba
Attorney, Agent, or Firm—Birch, Stewart, Kolasch & Birch

[57] ABSTRACT

A solid base which is obtainable by reacting alumina with an alkali metal hydroxide and an alkali metal hydride or reacting water-containing alumina with an alkali metal hydride in an amount more than the molar equivalent of water container in the water-containing alumina, at a temperature of 200° to 500° C. in an inert gas atmosphere can effectively catalyze various reactions, particularly isomerization of olefins.

21 Claims, No Drawings

SOLID BASE, PROCESS FOR PREPARING THE SAME AND USE OF THE SAME IN PREPARATION OF INTERNAL OLEFINS

This application is a divisional of copending application Ser. No. 155,848 filed on Feb 16, 1988 now U.S. Pat. No 4,822,764

BACKGROUND OF THE INVENTION

1. Field of the Invention

The present invention relates to a solid base, a process for preparing the same and use of the same in the preparation of internal olefins. More particularly, it relates to a solid base obtainable by reacting alumina, an alkali metal hydroxide and an alkali metal hydride at a specific temperature in an inert gas atmosphere or by reacting water-containing alumina and an alkali metal hydride in a specific ratio at a specific temperature in an inert gas atmosphere, a process for preparing said solid base and a process for preparing an internal olefin by the use of said solid base.

2. Description of the Prior Art

A solid base is useful as a catalyst used, for example, in isomerization of olefins, hydrogenation and dehydrogenation.

For example, an alkali metal dispersed on an anhydrous carrier with a large surface area (e.g., activated carbon, silica gel, alumina and the like) is a known solid base (cf. J. Am. Chem. Soc., 82, 387 (1960)). However, the dispersion catalyst has unsatisfactory handleability and less safety since it ignites and loses its activity on contact with air. Further, the dispersion catalyst has unsatisfactory catalytic activity.

The present inventors have proposed a solid base which is prepared from alumina, an alkali metal hydroxide and an alkali metal or from water-containing alumina and an alkali metal. The solid base has more excellent catalytic activity and a higher stability to air than the alkali metal dispersion catalyst (cf. Japanese Patent Publication Nos. 3274/1975 and 21378/1982 and U.S. Pat. Nos. 3,808,152, 3,897,509 and 3,928,485). However, such solid base is still unsatisfactory since the alkali metal should be used for its preparation and its catalytic activity is not satisfactory.

Also known is a base catalyst comprising an alkali metal hydride (cf. Japanese Patent Kokai Publication Nos. 121753/1978 and 134736/1984). Since the alkali metal hydride can act as a catalyst in the presence of ammonia or hydrazine, it has some drawbacks such that a purification apparatus for separating and removing ammonia or hydrazine is required and the catalytic reaction is troublesome due to the use of ammonia or hydrazine.

SUMMARY OF THE INVENTION

One object of the present invention is to provide a solid base with improved catalytic performances.

Another object of the present invention is to provide a solid base with improved stability and performances formed from alumina, an alkali metal hydroxide and an alkali metal hydride or water-containing alumina and an alkali metal hydride.

Further object of the present invention is to provide a process for preparing an internal olefin by the use of a solid base of the present invention.

These and other objects are accomplished by a solid base according to the present invention which is obtainable by reacting alumina with an alkali metal hydroxide and an alkali metal hydride or reacting water-containing alumina with an alkali metal hydride in an amount more than the molar equivalent of water contained in the water-containing alumina, at a temperature range of from 200° to 500° C. in an inert gas atmosphere.

DETAILED DESCRIPTION OF THE INVENTION

In the first embodiment of the present invention, the solid base is prepared by reacting alumina with an alkali metal hydroxide and an alkali metal hydride.

Examples of the alkali metal hydroxide are lithium hydroxide, sodium hydroxide, potassium hydroxide, rubidium hydroxide and cesium hydroxide and mixtures thereof. It may be used in a solid or liquid state or in the form of an aqueous solution.

As the alkali metal hydride, a hydride of an alkali metal of Group I of the Periodic Table such as sodium, potassium and lithium is used. The alkali metal hydrides may be used as a mixture of two or more of them.

As a combination of the alkali metal hydroxide and the alkali metal hydride, a combination of an alkali metal hydroxide and its corresponding hydride, for example, a combination of sodium hydroxide and sodium hydride, of potassium hydroxide and potassium hydride and the like is preferably used, although a combination of an alkali metal hydroxide and a hydride of other alkali metal, for example, a combination of potassium hydroxide and sodium hydride or of sodium hydroxide and potassium hydride may be used. From a practical approach, a combination of sodium hydroxide and sodium hydride is used.

An amount of the alkali metal hydroxide is 5 to 40% by weight, and an amount of the alkali metal hydride is 2 to 10% by weight, preferably 4 to 9% by weight, both based on the weight of alumina in view of the catalytic activity of the prepared solid base.

Usually, alumina with a relatively large surface area such as $\chi$-, $\sigma$-, $\eta$-, $\gamma$-, $\delta$-, $\kappa$- and $\theta$-alumina is used. Among them, $\gamma$-, $\chi$-, $\rho$- and $\eta$-alumina are preferred in view of the catalytic activity. Since alumina acts as a carrier as well as a reactant with the alkali metal hydroxide and the alkali metal hydride, an alumina-containing compound such as kaolin and alumina silicate may be used in place of alumina. However, the use of alumina is preferred.

According to the present invention, alumina, the alkali metal hydroxide and the alkali metal hydride are reacted at a specific temperature in an inert gas atmosphere as described above to prepare the solid base with improved properties. As to the preferred sequence of the reactions, alumina and the alkali metal hydroxide are first reacted and followed by reacting the reaction product with the alkali metal hydride.

As the inert gas, nitrogen, helium, argon and the like can be used.

In the present invention, the properties of the prepared solid base are influenced by the reaction temperatures. Particularly, the catalytic activity of the solid base is greatly affected by the temperature at which the alkali metal hydride is reacted.

Alumina and the alkali metal hydroxide are reacted at a temperature range of from 200° to 500° C., preferably from 250° to 450° C., and the alkali metal hydride is reacted at a temperature range of from 200° to 500° C., preferably from 250° to 450° C., more preferably from 280° to 380° C. By reacting the compounds at such temperatures, the solid base prepared is characterized with a significantly high catalytic activity in comparison with the conventional solid bases. Therefore, even in a small amount, the solid base of the present invention can effectively catalyze objective reactions.

The reaction time varies with other reaction conditions such as temperature. The reaction of alumina and the alkali metal hydroxide may be completed within 0.5 to 10 hours, and the subsequent reaction of the reaction product with the alkali metal hydride may be completed within 10 to 300 minutes.

In addition to the above method, according to the present invention, the solid base can be prepared by reacting water-containing alumina with an alkali metal hydride.

Various types of water-containing alumina can be used except for $\alpha$-alumina.

Generally, alumina is produced by calcining aluminum hydroxide. According to the calcining temperature and time, alumina has various metastable states and a water content varies so that various type of alumina are produced. In the present invention, such alumina may be used. Preferably, water-containing alumina with a large surface area such as $\gamma$-, $\chi$-, $\rho$- and $\eta$-alumina are used.

Although it is rather difficult to measure the water content of alumina, the water content may be determined by weight loss upon heating during a heating period in which alumina in its original state is changed to $\alpha$-alumina which contains no removable water. Usually, the water content of water-containing alumina is 1.2 to 10% by weight, preferably 2 to 7% by weight in terms of weight loss upon heating.

The alkali metal hydride used in this preparation is the same as described above, and preferably sodium hydride, potassium hydride and lithium hydride. A total amount of the alkali metal hydride to be reacted is greater than the amount which corresponds to a molar equivalent of water contained in alumina. Preferably, the alkali metal hydride is used in an amount of 1.01 to 2 time molar equivalents of water contained in alumina in total.

According to the present invention, the alkali metal hydride may be reacted in one portion with the water-containing alumina, or the alumina water-containing alumina is reacted with the first portion of the alkali metal hydride in an amount of not more than the molar equivalent of water contained in alumina, for example, an amount that corresponds to 0.2 to 1 time molar equivalent of water, and then the second portion of the alkali metal hydride is reacted with the reaction product. In the latter case, a type of alkali metal hydride first reacted and the type of alkali metal hydride subsequently reacted may be the same or different. The alkali metal hydride is commercially available in the form of a powder or a dispersion in an inert medium such as mineral oil. When the dispersion of alkali metal hydride in the inert medium is used, it may be added to the reaction mixture as such or after removing the medium.

As the inert gas, the above described gases are used.

Also in this second preparation of a solid base, the reaction temperatures, particularly in the above latter manner, the reaction temperature in the second step, have significant influences on the properties of the solid base formed.

A reaction temperature range is from 200° to 500° C., preferably 250° to 450° C., more preferably 280° to 380° C.

By reacting the compounds at such temperatures, a solid base having a significantly high catalytic activity is prepared. Therefore, even in a small amount, the base of the present invention can effectively catalyze objective reactions.

The reaction time varies with other reaction conditions such as the reaction temperature. Usually, it is from 15 minutes to 10 hours.

According to the present invention, the solid base is prepared from the alkali metal hydride which is easily handled and has much higher catalytic activity in the absence of any aid such as ammonia and hydrazine. Further, the solid base prepared by the present invention can effectively catalyze various reactions even in a small amount.

For example, the solid base of the present invention can be used to catalyze isomerization of olefins, condensation reactions which are promoted by a base, and the like. Among these reactions, isomerization of olefins is significantly catalyzed by the solid base of the present invention. For example, isomerization of a terminal olefin to a more stable internal olefin is effectively catalyzed.

Now, the preparation of internal olefins by the use of the solid base of the present invention is explained.

Examples of olefins to be isomerized are terminal olefins such as unsaturated aliphatic compounds (e.g. 1-butene, 1-pentene, 1-hexene, 1-heptene, 1-nonene, 1-decene, 2-methyl-1-butene, 3-methyl-1-butene, 4-metyl-1-pentene, 3methyl-1-pentene, 2-methyl-1-pentene, 2,3-dimethyl-1-butene, etc.), aromatic compounds (e.g. allylbenzene, allyltoluene, etc.), bridged ring compounds (2-isopropenylnorbornane, 5-isopropenyl-2-norbornene, 5-vinyl-2-norbornene, 6-methyl-5-vinylnorborane, etc.), cyclic compounds (e.g. methylenecyclopentane, methylenecyclohexane, etc.), diolefins (e.g. 1,4-pentadiene, 1,5-hexadiene, 2,5-dimethyl-1,4-hexadiene, 2,5-dimethyl-1,5-hexadiene, etc.); and compounds having an internal double bond which can be isomerized to a more stable position (e.g. 4-methyl-2-pentene, 5-(2-propenyl)-2-norbornene, etc.).

In the preparation of internal olefin, the amount of solid base catalyst to be used is from 1/3,000 to 1/20, preferably from 1/2,000 to 1/50 part by weight per part of the raw material olefin. It is not necessarily required to heat the reaction system since isomerization proceeds at room temperature, although the reaction system may be heated. Usually, the isomerization temperature is from $-30°$ to 120° C., preferably from $-10°$ to $+100°$ C.

Optionally, an inert solvent may be used. Examples of the inert solvent are hydrocarbons such as pentane, hexane, heptane and dodecane. Preferably, the isomerization is carried out in the absence of the solvent or in the presence of a solvent which can be a solvent in a subsequent step.

The isomerization is carried out batch wise or continuously. Preferably, the raw material olefin is pretreated with a drying agent such as alumina. For assuring the complete proceeding of reaction, the isomerization may be carried out in an atmosphere of an inert gas such as nitrogen, helium and argon.

The isomerization product is usually analyzed by such method as gas chromatography and isolated from the catalyst by a conventional manner such as filtration or decantation.

According to the present invention, the solid base is prepared by using the alkali metal hydride which is easily handled, and moreover it has high catalytic activity without using ammonia or hydrazine. Thus, a small amount of the solid base can effectively isomerize the olefin to give the internal olefin with a high yield without the formation of by-products such as polymerized materials.

Practically and presently preferred embodiments of the present invention will be illustrated by following examples.

EXAMPLE 1

To a 100 ml flask, γ-alumina (26.6 g) was added and heated to 500° C. under nitrogen with stirring at the same temperature for one hour. After cooling to 330° C., sodium hydroxide (2.5 g) was added thereto and stirred at the same temperature for 3 hours.

Then, sodium hydride (1.23 g) was added. Before the addition, sodium hydride which was commercially available was washed with hexane under nitrogen and filtered to remove the mineral oil and dried. The reaction mixture was heated to 330° C. with stirring and further stirred at the same temperature for one hour. Then, it was cooled to room temperature to obtain a solid base (27.8 g).

EXAMPLES 2-5 and COMPARATIVE EXAMPLES 1-3

In the same manner as in Example 1 but using alumina, alkali metal hydroxide, alkali metal hydride and reaction conditions shown in Table 1, each solid base was prepared.

TABLE 1

| Example No. | Alumina (g) | Addition conditions of alkali metal hydroxide | | | Addition conditions of alkali metal hydride | | | Yield of solid base (g) |
|---|---|---|---|---|---|---|---|---|
| | | MOH (g) | Temp. (°C.) | Stirring time (hr) | MH (g) | Temp. (°C.) | Stirring time (hr) | |
| 2 | x-Alumina (31.6) | KOH (4.5) | 380 | 3 | NaH (1.58) | 380 | 1 | 35.1 |
| 3 | γ-Alumina (26.6) | NaOH (2.5) | 350 | 3 | KH (2.23) | 350 | 1 | 29.0 |
| 4 | γ-Alumina (26.6) | NaOH (2.5) | 300 | 3 | NaH (1.28) | 250 | 3 | 28.2 |
| 5 | γ-Alumina (26.6) | NaOH (2.5) | 350 | 3 | NaH (2.22) | 350 | 1 | 29.0 |
| Com. 1 | γ-Alumina (26.6) | NaOH (2.5) | 320 | 3 | NaH (1.28) | 25 | 1 | 28.4 |
| Com. 2 | γ-Alumina (26.6) | NaOH (2.5) | 330 | 3 | NaH (1.28) | 170 | 1 | 28.3 |
| Com. 3 | γ-Alumina (26.6) | NaOH (2.5) | 510 | 2 | NaH (1.28) | 510 | 1 | 27.8 |

EXAMPLE 6

To a 200 ml flask in nitrogen atmosphere, the solid base prepared in Example 1 (0.19 g) and then 5-vinyl-2norbornene (hereinafter referred to as "VNB") (purity, 99.9%) (97.1 g) were added and the resultant mixture was stirred at a temperature of 15°–20° C. for 20 hours. Thereafter, the catalyst was filtered off to obtain a reaction mixture (96.2 g). Gas chromatographic analysis of the mixture revealed that 99.4% of 5-ethylidene-2-norbornene (hereinafter referred to as "ENB") and 0.5% of VNB were contained in the product.

EXAMPLES 7-10 AND COMPARATIVE EXAMPLES 4-6

In the same manner as in Example 6 but using the solid base and reaction conditions shown in Table 2, VNB was isomerized to ENB. The results are also shown in Table 2.

TABLE 2

| Example No. | Solid base (g) | Amount of VNB (g) | Reaction conditions | | Reaction results | |
|---|---|---|---|---|---|---|
| | | | Temp. (°C.) | Time (hrs) | ENB (%) | VNB (%) |
| 7 | Example 2 (0.22) | 55.1 | 15–20 | 7 | 99.5 | 0.4 |
| 8 | Example 3 (0.21) | 69.4 | 15–20 | 4 | 99.2 | 0.7 |
| 9 | Example 4 (0.21) | 30.5 | 15–20 | 10 | 99.1 | 0.8 |
| 10 | Example 5 (0.20) | 26.0 | 15–20 | 24 | 99.0 | 0.9 |
| Comp. 4 | Com. Ex. 1 (0.20) | 10.0 | 15–20 | 24 | 0 | 99.9 |
| Comp. 5 | Com. Ex. 2 (0.21) | 10.5 | 15–20 | 24 | 0.1 | 99.8 |
| Comp. 6 | Com. Ex. 3 (0.19) | 9.6 | 15–20 | 24 | 79.2 | 20.7 |

EXAMPLE 11

To a 100 ml flask in nitrogen atmosphere, the solid base prepared in Example 1 (0.22 g) and then 5-isopropenyl-2-norbornene (10.1% of exo form and 89.9% of endo form) (26.4 g) were added and stirred at a temperature of 15°–20° C. for 16 hours. Gas chromatographic analysis of the resulting reaction mixture revealed that 99.2% of 5-isopropylidene-2-norbornene and 0.3% of exo-5-isopropenyl-2-norbornene were contained in the product.

EXAMPLE 12

A tube of 5 mm in inner diameter and 100 mm in length equipped with an outer jacket was filled with the solid base prepared in Example 1 (0.94 g) in nitrogen atmosphere. VNB (purity, 99.9 %) was flowed from the upper end of the tube at a flow rate of 3.4 g/hr. with circulating cooling water kept at 15° to 20° C. in the jacket.

The effluent from the lower end of the tube was analyzed. The composition of the effluent was as follows:

| Time (hrs.) | VNB (%) | ENB (%) |
|---|---|---|
| 15 | 0.3 | 99.5 |
| 25 | 0.3 | 99.5 |
| 35 | 0.3 | 99.5 |
| 45 | 0.3 | 99.4 |

The total amount of effluent was 150.9 g and an average purity of ENB was 99.5%.

EXAMPLE 13

In a 100 ml flask in nitrogen atmosphere, the solid base prepared in Example 1 (0.25 g) and then 4-methyl1-pentene (20.1 g) were charged and the resultant mixture was stirred at a temperature of 15°-20° C. for 16 hours. Gas chromatographic analysis of the resulting reaction mixture revealed that 90.6% of 2-methyl-2-pentene, 8.8 % of 4- methyl-2-pentene and 0.4% of 4-methyl-1-pentene were contained in the mixture.

EXAMPLE 14

To a 200 ml flask in nitrogen atmosphere, the solid base prepared in Example 3 (0.25 g) and then 4-methyl-1-pentene (37.7 g) were added and stirred at a temperature of 15°-20° C. for 8 hours. Gas chromatographic analysis of the resulting reaction mixture revealed that 90.2% of 2-methyl2-pentene, 9.3% of 4-methyl-2-pentene and 0.3% of 4-methyl-1-pentene were contained in the mixture.

COMPARATIVE EXAMPLE 7

To a 100 ml flask in nitrogen atmosphere, the solid base prepared in Comparative Example 2 (0.30 g) and then 4-methyl-1-pentene (7.0 g) were added and stirred at a temperature of 15°-20° C. for 48 hours. Gas chromatographic analysis of the resulting reaction mixture revealed that 90.2% of 4-methyl-1-pentene, 6.2% of 4-methyl-2-pentene and 3.6% of 2-methyl-2-pentene were contained in the mixture.

Comparative EXAMPLE 8

To a 100 ml flask in nitrogen atmosphere, the solid base prepared in Comparative Example 3 (0.31 g) and then 4-methyl-1-pentene (15.5 g) were added and stirred at a temperature of 15°-20° C. for 48 hours. Gas chromatographic analysis of the resulting reaction mixture revealed that 0.7% of 4-methyl-1-pentene, 31.2% of 4-methyl-2-pentene and 68.0% of 2-methyl-2-pentene were contained in the mixture.

EXAMPLE 15

In a 100 ml flask, γ-alumina containing 2.2% by weight of water (25.0 g) was charged and then, in nitrogen atmosphere, sodium hydride (1.28 g) was added thereto. The resultant mixture was heated to 350° C. with stirring and further stirred at the same temperature for one hour. It was cooled to room temperature to obtain a solid base (25.9 g).

EXAMPLES 16–20 AND COMPARATIVE EXAMPLES 9–11

In the same manner as in Example 15 but carrying out the reaction under the conditions specified in Table 3, a solid base was prepared.

TABLE 3

| Example No. | Alumina Water content (%) | Alumina Amount (g) | MH (g) | Reaction conditions of alkali metal hydrides Temp. (°C.) | Time (hrs) | Yield of solid base (g) |
| --- | --- | --- | --- | --- | --- | --- |
| 16 | 2.2 | 25.0 | NaH (1.28) | 250 | 3 | 26.0 |
| 17 | 2.2 | 25.0 | NaH (1.28) | 450 | 1 | 25.9 |
| 18 | 1.2 | 25.0 | NaH (0.78) | 350 | 1 | 25.6 |
| 19 | 2.2 | 25.0 | KH (2.23) | 350 | 1 | 26.8 |
| 20 | 1.2 | 25.0 | NaH (1.28) | 350 | 1 | 26.0 |
| Comp. 9 | 2.2 | 25.0 | NaH (1.28) | 25 | 1 | 26.2 |
| Comp. 10 | 2.2 | 25.0 | NaH (1.28) | 170 | 1 | 26.2 |
| Comp. 11 | 2.2 | 25.0 | NaH (1.28) | 510 | 1 | 25.8 |

EXAMPLES 21

To a 200 ml flask in nitrogen atmosphere, the solid base prepared in Example 15 (0.13 g) and then VNB (purity, 99.9%) (65.0 g) were added and the resultant mixture was stirred at a temperature of 15°-20° C. for 15 hours. Thereafter, the catalyst was filtered off to give a reaction product (64.3 g). Gas chromatographic analysis of the product revealed that 99.6% of ENB and 0.3% of VNB were contained in the mixture.

EXAMPLES 22–26 AND COMPARATIVE EXAMPLES 12–14

In the same manner as in Example 21 but using the solid base and reaction conditions shown in Table 4, VNB was isomerized to ENB. The results are also shown in Table 4.

TABLE 4

| Example No. | Solid base (g) | Amount of VNB (g) | Reaction conditions Temp. (°C.) | Reaction conditions Time (hrs) | Reaction results ENB (%) | Reaction results VNB (%) |
| --- | --- | --- | --- | --- | --- | --- |
| 22 | Example 16 (0.22) | 30.0 | 15–20 | 10 | 99.1 | 0.8 |
| 23 | Example 17 (0.15) | 21.0 | 15–20 | 16 | 99.4 | 0.5 |
| 24 | Example 18 (0.12) | 18.6 | 15–20 | 24 | 99.2 | 0.7 |
| 25 | Example 19 (0.14) | 44.7 | 15–20 | 4 | 99.2 | 0.5 |
| 26 | Example 20 (0.20) | 17.0 | 15–20 | 20 | 91.8 | 8.1 |
| Comp. 12 | Com. Ex. 9 (0.14) | 8.6 | 15–20 | 24 | 0 | 99.9 |
| Comp. 13 | Com. Ex. 10 (0.26) | 14.2 | 15–20 | 24 | 0.1 | 99.8 |
| Comp. 14 | Com. Ex. 11 (0.27) | 13.9 | 15–20 | 20 | 87.4 | 12.5 |

EXAMPLE 27

To a 100 ml flask in nitrogen atmosphere, the solid base prepared in Example 15 (0.24 g) and then 5-isopropenyl-2-norbornene (10.1% of exo form and 89.9% of endo form) (28.9 g) were added and stirred at a temperature of 15°-20° C. for 20 hours. Gas chromatographic analysis of the resulting reaction mixture revealed that 99.3% of 5-isopropylidene-2-norbornene, 0.3% of exo-5-isopropenyl-2-norbornene and less than 0.1% of endo-5-isopropynyl-2-norbornene were contained in the product.

EXAMPLE 28

A tube of 5 mm in inner diameter and 100 mm in length equipped with an outer jacket was filled with the solid base prepared in Example 15 (0.95 g) in nitrogen atmosphere. VNB (purity, 99.9 %) was flowed from the upper end of the tube at a flow rate of 3.4 g/hr. with circulating cooling water kept at 15° to 20° C. in the jacket.

The effluent from the lower end of the tube was analyzed. The composition of the effluent was as follows:

| Time (hrs.) | VNB (%) | ENB (%) |
|---|---|---|
| 15 | 0.3 | 99.5 |
| 25 | 0.3 | 99.5 |
| 35 | 0.3 | 99.5 |
| 45 | 0.3 | 99.5 |

The total amount of effluent was 152.1 g and an average content of ENB was 99.5%.

EXAMPLE 29

To a 100 ml flask in nitrogen atmosphere, the solid base prepared in Example 15 (0.25 g) and then 4-methyl-1-pentene (23.0 g) were added and the resultant mixture was stirred at a temperature of 15°-20° C. for 16 hours. Gas chromatographic analysis of the product revealed that 90.2% of 2-methyl-2-pentene, 9.2% of 4-methyl-2-pentene and 0.4% of 4-methyl-1-pentene were contained in the product.

EXAMPLE 30

To a 200 ml flask in nitrogen atmosphere, the solid base prepared in Example 19 (0.24 g) and then 4- methyl-1-pentene (36.2 g) were added and the resultant mixture was stirred at a temperature of 15°-20° C. for 8 hours. Gas chromatographic analysis of the product revealed that 9.9% of 2-methyl-2-pentene, 9.8% of 4-methyl-2-pentene and 0.3% of 4-methyl-1-pentene were contained in the product.

COMPARATIVE EXAMPLE 15

To a 100 ml flask in nitrogen atmosphere, the solid base prepared in Comparative Example 10 (0.30 g) and then 4-methyl-1-pentene (6.4 g) were added and the resultant mixture was stirred at a temperature of 15°-20° C. for 48 hours. Gas chromatographic analysis of the product revealed that 89.3% of 4-methyl-1-pentene, 6.8% of 4-methyl-2pentene and 3.9% of 2-methyl-2-pentene were contained in the product.

COMPARATIVE EXAMPLE 16

To a 100 ml flask in nitrogen atmosphere, the solid base prepared in Comparative Example 11 (0.30 g) and then 4-methyl-1-pentene (15.3 g) were added and the resultant mixture was stirred at a temperature of 15°-20° C. for 48 hours. Gas chromatographic analysis of the product revealed that 0.6% of 4-methyl-1-pentene, 27.9% of 4-methyl-2pentene and 71.1% of 2-methyl-2-pentene were contained in the product.

What is claimed is:

1. A process for preparing an internal olefin comprising isomerizing an olefin in the presence of a catalyst comprising a solid base which is obtainable by reacting alumina with an alkali metal hydroxide and an alkali metal hydride or reacting water-containing alumina with an alkali metal hydride in an amount more than the molar equivalent of water contained in the water-containing alumina, at a temperature of 200° to 500° C. in an inert gas atmosphere.

2. The process according to claim 1, wherein the solid base is obtainable by reacting alumina with an alkali metal hydroxide and an alkali metal hydride.

3. The process according to claim 2, wherein the alumina and the alkali metal hydroxide is reacted at a temperature of 250° to 450° C.

4. The process according to claim 2, wherein the alkali metal hydride is reacted with a reaction product of the alumina and the alkali metal hydroxide at a temperature of 250° to 450° C.

5. The process according to claim 2, wherein the alkali metal hydroxide is selected from the group consisting of lithium hydroxide, sodium hydroxide, potassium hydroxide, rubidium hydroxide, cesium hydroxide and mixtures thereof.

6. The process according to claim 2, wherein the alkali metal hydride is selected from the group consisting of sodium hydride, potassium hydride and lithium hydride.

7. The process according to claim 2, wherein an amount of the alkali metal hydroxide is from 5 to 40% by weight based on the weight of alumina.

8. The process according to claim 2 wherein an amount of the alkali metal hydride is from 2 to 10% by weight based on the weight of alumina.

9. The process according to claim 2, wherein the alumina is selected from the group consisting of $\gamma$-alumina, $\chi$-alumina, $\rho$-alumina and $\eta$-alumina and mixtures thereof.

10. The process according to claim 1, wherein the solid base is obtainable by reacting a water-containing alumina with an alkali metal hydride.

11. The process according to claim 10, wherein the water-containing alumina and the alkali metal hydride is reacted at a temperature of 250° to 450° C.

12. The process according to claim 10, wherein the alkali metal hydride is selected from the group consisting of sodium hydride, potassium hydride and lithium hydride.

13. The process according to claim 10, wherein the water-containing alumina is reacted with the alkali metal hydride in an amount of 1.01 to 2 time molar equivalents of water contained in the alumina.

14. The process according to claim 10, wherein the alkali metal hydride is added in two portions, the first one of which is in an amount not more than a molar equivalent of water contained in the water-containing alumina and the second one of which is the rest of the alkali metal hydride.

15. The process according to claim 10, wherein the first portion of the alkali metal hydride is used in an amount of 0.2 to 1 time molar amount of water contained in the alumina.

16. The process according to claim 10, wherein the alkali metal hydride is added in one portion and reacted with the water-containing alumina.

17. The process according to claim 10, wherein the alumina is one selected from the group consisting of water-containing $\gamma$-alumina, $\chi$-alumina, $\rho$-alumina and $\eta$-alumina.

18. The process according to claim 10, wherein the water content of the water-containing alumina is 1.2 to 10% by weight.

19. The process according to claim 1, wherein the solid base is used in an amount of from 1/2,000 to 1/50 parts by weight per part of the olefin.

20. The process according to claim 1, wherein the isomerization temperature is in a range of from $-10°$ to $+100°$ C.

21. The process according to claim 1, wherein the olefin to be isomerized is a member selected from the group consisting of 1-butene, 1-pentene, 1-hexene, 1-heptene, 1-nonene, 1-decene, 2-methyl-1-butene, 3-methyl-1-butene, 4-methyl-1-butene, 3-methyl-1-pentene, 2-methyl-1-pentene, 2,3-dimethyl-1-butene, allylbenzene, allyltoluene, 2-isopropenylnorbornane, 5-isopropenyl-2-norbornene, 5-vinyl-2-norbornene, 6-methyl-5-vinylbornene, methylenecyclopentane, methylenecyclohexane, 1,4-pentadiene, 1,5-hexadiene, 2,5-dimethyl-1,4-hexadiene, 2,5-dimethyl-1,5-hexadiene, 4-methyl-2-pentene, and 5-(2-propenyl)-2-norbornene.

* * * * *